United States Patent
Naganawa et al.

(10) Patent No.: US 6,339,954 B1
(45) Date of Patent: Jan. 22, 2002

(54) METHOD OF ANALYZING CONCENTRATION OF TARGET SUBSTANCE USING QUARTZ OSCILLATOR AND DEVICE THEREFOR

(75) Inventors: Ryuichi Naganawa; Kazutoshi Noda; Hiroaki Tao; Mamoru Tominaga, all of Tsukuba (JP)

(73) Assignee: Secretary of Agency of Industrial Science and Technology (JP)

( * ) Notice: Subject to any disclaimer, the term of this patent is extended or adjusted under 35 U.S.C. 154(b) by 0 days.

(21) Appl. No.: 09/531,430

(22) Filed: Mar. 20, 2000

(30) Foreign Application Priority Data

Apr. 16, 1999 (JP) .......................................... 11-108949

(51) Int. Cl.[7] .......................... G01N 29/00; G01N 29/02
(52) U.S. Cl. ...................................... 73/61.79; 73/24.06
(58) Field of Search ............................ 73/24.06, 61.79, 73/61.43, 61.45, 61.49; 310/343, 313; 200/61.04; 340/605

(56) References Cited

U.S. PATENT DOCUMENTS

| | | | | |
|---|---|---|---|---|
| 4,259,606 A | * | 3/1981 | Vig | 310/343 |
| 4,414,441 A | * | 11/1983 | Perry et al. | 200/61.04 |
| 4,590,462 A | * | 5/1986 | Moorehead | 340/605 |
| 5,852,229 A | * | 12/1998 | Josse et al. | 73/24.06 |

FOREIGN PATENT DOCUMENTS

| | | | | |
|---|---|---|---|---|
| EP | 1045243 A2 | * | 10/2000 | G01N/5/02 |
| JP | 410038784 A | * | 2/1998 | G01N/5/02 |

* cited by examiner

Primary Examiner—Hezron Williams
Assistant Examiner—Jay L. Politzer
(74) Attorney, Agent, or Firm—Lorusso & Loud

(57) ABSTRACT

In a method of analyzing a concentration of a target substance contained in a fluid using a quartz oscillator having a surface covered with a layer capable of absorbing the target substance, the temperature of the fluid and the quartz oscillator is controlled at substantially the same predetermined temperature selected according to the concentration of the target substance in said fluid, so that the analysis can be made with optimum sensitivity. A device for analyzing a concentration of a target substance contained in a fluid, includes a contacting chamber accommodating a quartz oscillator, a temperature controller, disposed in a feed passage for feeding the fluid into said contacting chamber, for adjusting a temperature of the fluid at a desired predetermined temperature; and a detector of a frequency of the quartz oscillator.

6 Claims, 2 Drawing Sheets

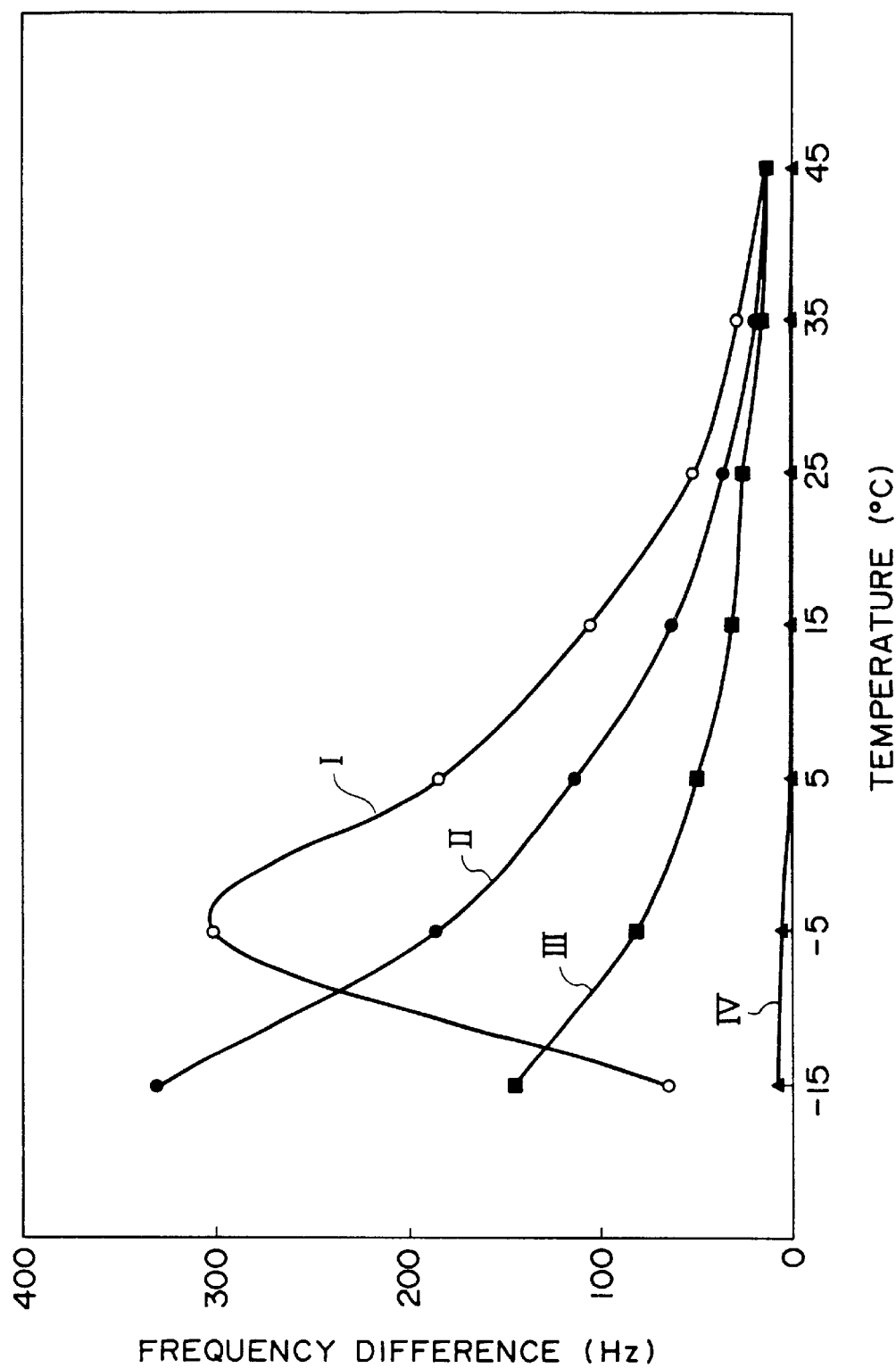

METHOD OF ANALYZING CONCENTRATION OF TARGET SUBSTANCE USING QUARTZ OSCILLATOR AND DEVICE THEREFOR

BACKGROUND OF THE INVENTION

This invention relates to a method of quantitatively analyzing a target substance, such as a harmful substance, contained in a liquid or a gas using a quartz oscillator and to a device therefor.

A gas analyzer using a quartz oscillator as a sensor is known (JP-A-08-233759, JP-A-10-038784 and JP-A-10-090152). The quartz oscillator has a lipid membrane capable of immobilizing a target substance contained in a fluid. Upon absorption of the target substance, the oscillation frequency is changed due to an increase of the weight of the lipid membrane. Thus, by detecting the change in frequency of the quartz oscillator, it is possible to determine the concentration of the target substance in the fluid. The conventional analyzer, however, has a drawback because the sensitivity of the sensor is not able to be changed. Thus, it has been hitherto necessary to concentrate or dilute the fluid so that the concentration of the target substance in the fluid falls within a range suitable for being detected by the analyzer.

SUMMARY OF THE INVENTION

It is, therefore, an object of the present invention to provide a method which can precisely analyze a concentration of a target substance contained in a fluid without need of any pretreatment, such as concentration or dilution, of the fluid, even when the concentration is extremely high or low.

Another object of the present invention is to provide a device for analyzing a concentration of a target substance contained in a fluid, which permits the control of the sensitivity thereof.

In accomplishing the foregoing objects, there is provided in accordance with one aspect of the present invention a method of analyzing a concentration of a target substance contained in a fluid, wherein said fluid is contacted with a quartz oscillator having a surface covered with a layer capable of absorbing the target substance so that the target substance is absorbed by said layer to cause a change in frequency of said quartz oscillator, and wherein said change in frequency of said quartz oscillator is detected to determine the concentration of said target substance, characterized in that said fluid and said quartz oscillator are controlled to have substantially the same temperature, and in that said temperature is selected so that said quartz oscillator has a desired sensitivity.

In another aspect, the present invention provides a method of analyzing a concentration of a target substance contained in a fluid, comprising the steps of:
(a) providing a quartz oscillator having a surface covered with a layer capable of absorbing the target substance;
(b) maintaining each of said fluid and said quartz oscillator at substantially the same predetermined temperature selected according to the concentration of the target substance in said fluid;
(c) contacting said fluid having said predetermined temperature with said layer of said quartz oscillator having said predetermined temperature, so that the target substance is absorbed by said layer; and
(d) detecting a frequency of said quartz oscillator during step (c).

In a further aspect, the present invention provides a device for analyzing a concentration of a target substance contained in a fluid, comprising:
a contacting chamber;
a feed passage for feeding the fluid into said contacting chamber;
means disposed in said feed passage for adjusting a temperature of said fluid at a desired predetermined temperature;
a discharge passage for discharging the fluid from said contacting chamber;
a quartz oscillator disposed in said chamber and having a surface covered with a layer capable of absorbing said target substance, so that the fluid introduced through said feed passage into said chamber is contacted with said layer; and
means for detecting a frequency of said quartz oscillator.

BRIEF DESCRIPTION OF THE DRAWINGS

Other objects, features and advantages of the present invention will become apparent from the detailed description of the preferred embodiments of the invention which follows, when considered in the light of the accompanying drawings, in which:

FIG. 2 is a graph showing temperature dependency of a frequency of various quartz oscillators having different lipid membranes.

DETAILED DESCRIPTION OF THE PREFERRED EMBODIMENTS OF THE INVENTION

Figure 1:
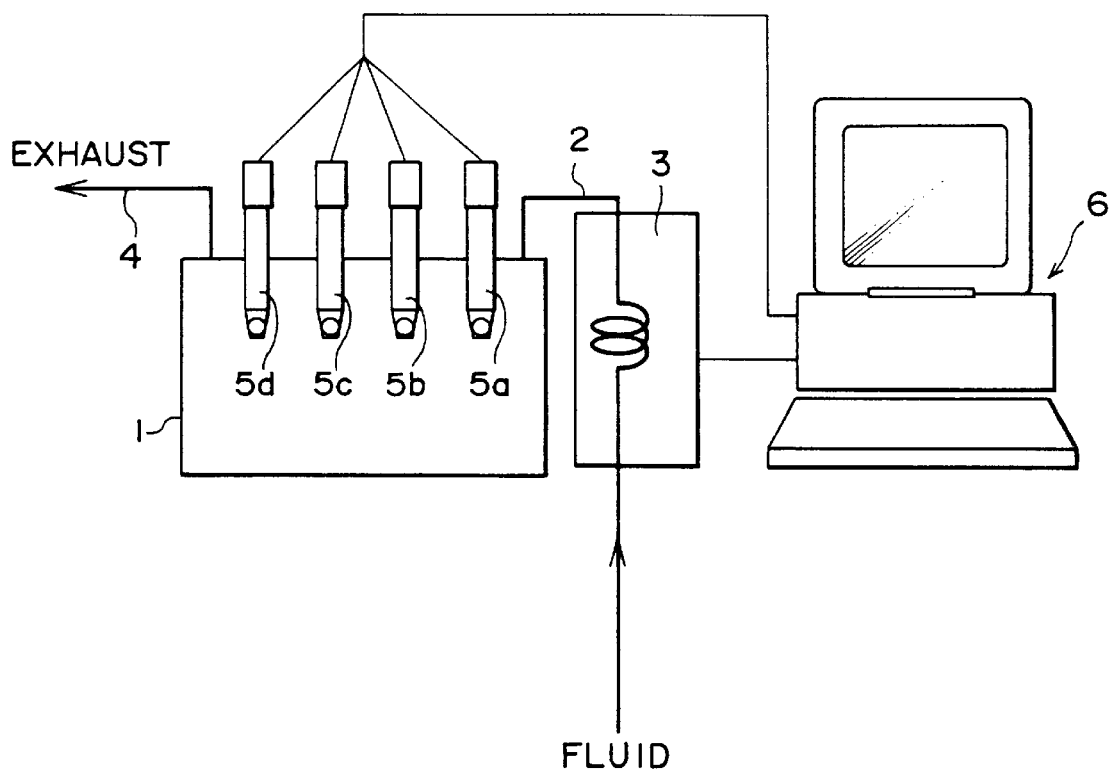
FIG. 1 is a schematic illustration of one embodiment of a device for analyzing a concentration of a target substance contained in a fluid in accordance with the present invention.

In the present invention, a quartz oscillator having a surface covered with a layer capable of absorbing a target substance is used as a detector for a target substance contained in a fluid. The oscillation frequency of the quartz oscillator varies with a change in weight of the layer caused by absorption and liberation of the target substance in the layer. By measuring the change of the oscillation frequency, therefore, it is possible to determine the concentration of the target substance in the fluid.

Any known quartz oscillator may be used for the purpose of the invention. Generally, however, a quartz detector having a fundamental frequency of 1–100 MHz, preferably 9–27 MHz is used.

The layer provided on the quartz oscillator can absorb or immobilize the target substance and may be, for example, a lipid membrane, a polar group-containing polymer membrane or a polymer matrix membrane containing an absorbent.

Examples of the lipids include as follows:
(1) A lipid represented by the formula:

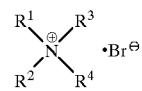

wherein $R^1$ and $R^2$ independently represent an alkyl or alkenyl group having 8–22, preferably 10–18 carbon atoms, $R^3$ represents an alkyl group having 1–8, preferably 1–6 carbon atoms and $R^4$ represents an alkenyl group having 1–8, preferably 1–6 carbon atoms.

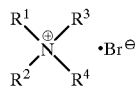

(2) A lipid represented by the formula:

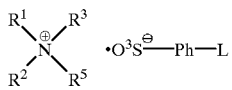

wherein $R^1$, $R^2$ and $R^3$ have the same meaning as above, $R^5$ represents an alkyl group having 1–8, preferably 1–6 carbon atoms, Ph represents a phenylene group and L represents a hydrocarbyl group such as a polyethylene chain.

(3) A lipid represented by the formula:

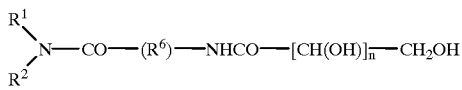

wherein $R^1$ and $R^2$ have the same meaning as above, $R^6$ represents an alkylene group having 2–8 carbon atoms and n is an integer of 1–10, preferably 2–6.

(4) A lipid represented by the formula:

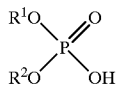

wherein $R^1$ and $R^2$ have the same meaning as above.

The foregoing lipids are suitable for absorbing volatile organic chlorine compounds such as trichloroethylene and tetrachloroethylene contained in a fluid.

The polar group of the polar group-containing polymers may be an acid group such as a carboxyl group, a sulfonic acid group or a phosphoric acid group or a basic group such as an amino group. The polymer containing acid groups is suitable for absorbing an alkaline gas such as ammonia or an amine contained in a gas, while the polymer containing basic groups is suitable for absorbing an acidic gas such as hydrogen chloride or sulfurous acid contained in a gas.

The absorbent to be dispersed in the polymer matrix membrane may be a porous inorganic absorbent or a polar group-containing low molecular weight compound. Examples of the porous absorbents include activated carbon, zeolite, alumina, silica, titania and silica-alumina. The porous absorbent is suitable for absorbing various kinds of compounds contained in a fluid. The polar groups of the low molecular weight compounds may be the same as those of the above-described polar group-containing polymer. The low molecular weight compound containing an acid group is suitable for absorbing an alkaline gas such as ammonia or an amine contained in a gas, while the low molecular weight compound containing a basic group is suitable for absorbing an acidic gas such as hydrogen chloride or sulfurous acid contained in a gas.

The polymer used with the absorbent may be any film forming resin used in the field of paint or coating material.

FIG. 1 diagrammatically illustrates a device for analyzing a concentration of a target substance contained in a fluid according to the present invention. Designated as 1 is a flow cell or a contacting chamber having a feed passage 2 for feeding the fluid into the contacting chamber 1. Heating and cooling means 3 is disposed in the feed passage 2 for adjusting a temperature of the fluid at a desired predetermined temperature of generally in the range of −15° C. to 45° C. The contacting chamber 1 also has a discharge passage 4 for discharging the fluid therethrough from the contacting chamber 1.

One or more quartz oscillators 5a–5d are disposed in the contacting chamber. Each oscillator has a surface covered with a layer capable of absorbing the target substance, as described previously. Thus, the fluid having the predetermined temperature is introduced through the feed passage 2 into the chamber 1 and is contacted with oscillators 5a–5d. Since the oscillators 5a–5d are disposed within the contacting chamber 1, the temperature of the oscillators 5a–5d is substantially the same as the fluid and, accordingly, is substantially equal to the predetermined temperature.

Each of the oscillators 5a–5d has an output (indicative of a frequency) coupled to a detector and a processing unit including a computer 6 where the concentration of the target gas is calculated from the frequency of each oscillator in the conventional manner.

The present invention is characterized in that each of the fluid containing a target substance and the quartz oscillator is controlled to have substantially the same predetermined temperature of generally in the range of −15° C. to 45° C. When the predetermined temperature is relatively high, namely 30 to 45° C., preferably 30 to 40° C., the absorbing capacity of the layer on the quartz oscillator is decreased and, therefore, the sensitivity of the oscillator is low. On the other hand, when the predetermined temperature is relatively low, namely −15 to 20° C., preferably −10 to 15° C., the absorbing capacity of the layer on the quartz oscillator is increased and, therefore, the sensitivity of the oscillator is high.

Thus, by suitably selecting the predetermined temperature controlled by the heating and cooling means 3, it is possible to select the optimum sensitivity for the quartz oscillator. For example, when the concentration of the target substance is found to be extremely high, the temperature controller 3 is actuated to increase the temperature of the fluid so that the sensitivity is lowered.

In the embodiment shown in FIG. 1, the temperature control for respective quartz oscillators 5a–5d is performed by controlling the temperature of the fluid (liquid or gas) containing the target substance by the heating and cooling means 3 at the predetermined temperature and by contacting each oscillator with the thus temperature-controlled fluid. Thus, the fluid passage 2 has a coiled portion made of a heat conductive material and accommodated in a thermostat chamber serving as the heating and cooling means. If desired, the oscillators 5a–5d, either separately or all together, may be accommodated in a temperature controlled box so that each oscillator is maintained at the predetermined temperature.

The following example will further illustrate the present invention.

EXAMPLE

A quartz oscillator of an AT-cut type having a fundamental frequency of 9 MHz was applied, on its one electrode, with a solution obtained by dissolving a lipid in dichloromethane in such an amount so that the oscillation frequency thereof decreased by about 5,000–15,000 Hz as a result of the coating (amount of the lipid was about 5 μg). The coating was dried in air. Similar procedure was repeated using different lipids, so that there were obtained four quartz oscillators (I)–(IV) having layers of lipids (I)–(IV). The lipids (I)–(IV) used are as shown below.

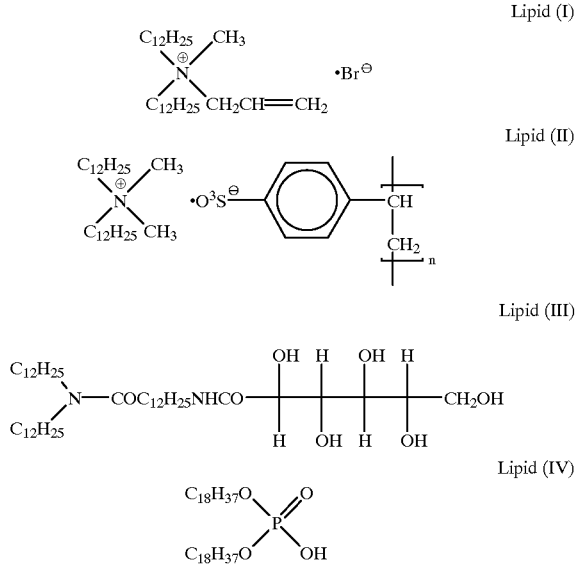

The four kinds of the thus prepared quartz oscillators having the layers of lipids (I)–(IV) were placed in a flow cell as shown in FIG. 1. Into the flow cell, nitrogen gas or nitrogen gas containing 1,000 ppm of trichloroethylene was introduced after controlling the temperature thereof at predetermined temperatures of −15, −5, 5, 15, 25, 35 and 45° C. The temperature control error was within ±0.3° C. While controlling the temperature of the gas and the quartz oscillator at above respective temperatures, the gas was fed to the flow cell as follows:

(1) nitrogen only was first fed to the flow cell;

(2) nitrogen gas containing 1,000 ppm of trichloroethylene was then fed to the flow cell;

(3) nitrogen only was then fed to the flow cell.

The frequency of each quartz oscillator 20 minutes after the commencement of the feed of trichloroethylene was measured. The difference in frequency at respective predetermined temperature is plotted in FIG. 2 in which the plots I–IV are for the quartz oscillators having the layers of lipids (I)–(IV), respectively. FIG. 2 indicates that the sensitivities at 45° C. and at −5° C. are about 0.3 and about 6 times as high as that at 25° C.

What is claimed is:

1. A method of analyzing a concentration of a target substance contained in a fluid, comprising the steps of:

(a) providing a quartz oscillator having a surface covered with a layer capable of absorbing the target substance;

(b) determining an optimum temperature providing the quartz oscillator with a desired sensitivity, the sensitivity of the quartz oscillator varying with temperature and with concentration of the target substance in the fluid;

(c) establishing a flow of the fluid;

(d) adjusting temperature of the fluid flow to the determined temperature;

(e) contacting said fluid having said predetermined temperature with said layer of said quartz oscillator having said predetermined temperature, so that the target substance is absorbed by said layer; and (f) detecting a frequency of said quartz oscillator during step (e).

2. A method as claimed in claim 1, wherein said predetermined temperature is in the range of between −15° C. and 45° C.

3. A method as claimed in claim 1 wherein said predetermined temperature is within one of the temperature ranges of between −10° C. and 15° C. and between 30° and 40°.

4. A method as claimed in claim 1, wherein said target substance is a chlorinated hydrocarbon.

5. A device for analyzing a concentration of a target substance contained in a fluid, comprising:

a contacting chamber;

a feed passage for feeding the fluid into said contacting chamber;

means disposed in said feed passage for adjusting a temperature of said fluid at a desired predetermined temperature;

a discharge passage for discharging the fluid from said contacting chamber;

a quartz oscillator disposed in said chamber and having a surface covered with a layer capable of absorbing said target substance, so that the fluid introduced through said feed passage into said chamber is contacted with said layer; and means for detecting a frequency of said quartz oscillator.

6. A device as claimed in claim 5, additionally comprising means surrounding said quartz oscillator for adjusting the temperature of said quartz oscillator at said predetermined temperature.

* * * * *